(12) United States Patent
Dalbow

(10) Patent No.: US 12,350,139 B2
(45) Date of Patent: Jul. 8, 2025

(54) SYSTEMS AND METHODS FOR HOLDING PROSTHETIC IMPLANTS

(71) Applicant: EDWARDS LIFESCIENCES CORPORATION, Irvine, CA (US)

(72) Inventor: Brendan Michael Dalbow, Huntington Beach, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 39 days.

(21) Appl. No.: 18/355,947

(22) Filed: Jul. 20, 2023

(65) Prior Publication Data
US 2023/0363882 A1     Nov. 16, 2023

Related U.S. Application Data

(63) Continuation of application No. PCT/US2022/013166, filed on Jan. 20, 2022.

(60) Provisional application No. 63/140,004, filed on Jan. 21, 2021.

(51) Int. Cl.
| A61F 2/00 | (2006.01) |
| A61F 2/24 | (2006.01) |
| B65D 25/10 | (2006.01) |
| B65D 65/38 | (2006.01) |
| B65D 77/20 | (2006.01) |

(52) U.S. Cl.
CPC .......... *A61F 2/0095* (2013.01); *A61F 2/2418* (2013.01); *B65D 25/10* (2013.01); *B65D 65/38* (2013.01); *B65D 77/20* (2013.01); *B65D 2565/388* (2013.01); *B65D 2577/2041* (2013.01)

(58) Field of Classification Search
CPC .. A61F 2/00; A61F 2/0095; A61F 2/24; A61F 2/2418; A61F 2/2427; B65D 25/10; B65D 65/38; B65D 77/20; B65D 2565/388; B65D 2577/2041
USPC .................................................. 206/438, 439
See application file for complete search history.

(56) References Cited

U.S. PATENT DOCUMENTS

| 4,011,947 A | 3/1977 | Sawyer |
| 4,101,031 A | 7/1978 | Cromie |
| 4,182,446 A | 1/1980 | Penny |
| 4,211,325 A | 7/1980 | Wright |
| 4,697,703 A | 10/1987 | Will |
| 4,801,015 A | 1/1989 | Lubock et al. |
| 5,167,223 A | 12/1992 | Koros et al. |
| 5,236,450 A | 8/1993 | Scott |
| 5,336,616 A | 8/1994 | Livesey et al. |
| 5,480,425 A | 1/1996 | Ogilive |
| 5,531,785 A | 7/1996 | Love et al. |

(Continued)

FOREIGN PATENT DOCUMENTS

| EP | 2921135 A1 | 9/2015 |
| WO | 2008035337 A2 | 3/2008 |
| WO | 2019212812 A1 | 11/2019 |

*Primary Examiner* — Bryon P Gehman
(74) *Attorney, Agent, or Firm* — Klarquist Sparkman, LLP; Linda Allyson Nassif

(57) ABSTRACT

Apparatuses, systems, and methods for holding prosthetic implants. The systems in certain embodiments may be for use in holding prosthetic implants prior to implantation within a patient's body and prior to coupling to a delivery apparatus used to implant the prosthetic implant within the patient's body. Certain embodiments disclosed herein may relate to apparatuses, systems, and methods for prosthetic implant preparation prior to implantation.

19 Claims, 13 Drawing Sheets

(56) References Cited

U.S. PATENT DOCUMENTS

| | | |
|---|---|---|
| 5,560,487 A | 10/1996 | Starr |
| 5,578,076 A | 11/1996 | Krueger et al. |
| 5,582,607 A | 12/1996 | Lackman |
| 5,615,770 A | 4/1997 | Applebaum et al. |
| 5,690,226 A | 11/1997 | N'Guyen |
| 5,720,391 A | 2/1998 | Dohm et al. |
| 5,776,187 A | 7/1998 | Krueger et al. |
| 5,800,531 A | 9/1998 | Cosgrove et al. |
| 5,823,342 A | 10/1998 | Caudillo et al. |
| 5,868,253 A | 2/1999 | Krueger et al. |
| 5,980,569 A | 11/1999 | Scirica |
| 5,984,959 A | 11/1999 | Robertson et al. |
| 6,090,138 A | 7/2000 | Chasak et al. |
| 6,126,007 A | 10/2000 | Kari et al. |
| 6,197,053 B1 | 3/2001 | Cosgrove et al. |
| 6,199,696 B1 | 3/2001 | Lytle et al. |
| 6,346,094 B2 | 2/2002 | West et al. |
| 6,416,547 B1 | 7/2002 | Erickson et al. |
| 6,534,004 B2 | 3/2003 | Chen et al. |
| 6,591,998 B2 | 7/2003 | Haynes et al. |
| 6,723,122 B2 | 4/2004 | Yang et al. |
| 6,736,845 B2 | 5/2004 | Marquez et al. |
| 6,966,925 B2 | 11/2005 | Stobie |
| 7,389,874 B2 | 6/2008 | Quest et al. |
| 7,699,168 B2 | 4/2010 | Ryan et al. |
| 7,712,606 B2 | 5/2010 | Salahieh et al. |
| 7,866,468 B2 | 1/2011 | Kyritsis |
| 8,652,145 B2 | 2/2014 | Maimon et al. |
| 9,114,010 B2 * | 8/2015 | Gaschino ............... A61F 2/2427 |
| 9,333,076 B1 * | 5/2016 | Edquist ................. A61F 2/2427 |
| 9,788,931 B2 * | 10/2017 | Giordano ............... A61F 2/2427 |
| 2002/0120328 A1 | 8/2002 | Pathak et al. |
| 2003/0070944 A1 | 4/2003 | Nigam |
| 2005/0241981 A1 | 11/2005 | Gupta et al. |
| 2006/0155363 A1 | 7/2006 | LaDuca et al. |
| 2006/0195183 A1 | 8/2006 | Navia et al. |
| 2008/0082163 A1 | 4/2008 | Woo |
| 2008/0177381 A1 | 7/2008 | Navia et al. |
| 2009/0130162 A2 | 5/2009 | Pathak et al. |
| 2009/0164005 A1 | 6/2009 | Dove et al. |
| 2011/0147251 A1 | 6/2011 | Hodshon et al. |
| 2013/0325111 A1 | 12/2013 | Campbell et al. |
| 2017/0056149 A1 | 3/2017 | Rajpara et al. |
| 2021/0030533 A1 * | 2/2021 | Tamir .................... A61F 2/2433 |

* cited by examiner

SYSTEMS AND METHODS FOR HOLDING PROSTHETIC IMPLANTS

CROSS-REFERENCE TO RELATED APPLICATIONS

This application is a continuation of PCT patent application no. PCT/US2022/013166 filed on Jan. 20, 2022, which claims the benefit of U.S. Provisional Application No. 63/140,004, filed Jan. 21, 2021, the entire contents of each of which are incorporated herein by this specific reference.

BACKGROUND

Field

Certain embodiments disclosed herein may relate to apparatuses, systems, and methods for holding prosthetic implants. The systems in certain embodiments may be for use in holding prosthetic implants prior to implantation within a patient's body and prior to coupling to a delivery apparatus used to implant the prosthetic implant within the patient's body. Certain embodiments disclosed herein may relate to apparatuses, systems, and methods for prosthetic implant preparation prior to implantation.

Background

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life-threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of prostheses including but not limited to replacement heart valves that can be compacted for delivery and then controllably expanded for controlled placement has proven to be particularly challenging. A delivery apparatus may be provided to deploy such an implant to the desired location in the human body. The implant may be in a compressed state when coupled to the delivery apparatus, and thus must be compressed for delivery to the desired location of implantation within the patient's body. The implant may be crimped to the delivery apparatus prior to insertion of the delivery apparatus into the patient's body.

Such implants may be transported to a clinician for the clinician's use to crimp the implant to a delivery apparatus prior to implantation within a patient's body. The implant is preferably not damaged upon transport to the clinician, and upon removal of the implant from a container for the implant prior to the crimping procedure. Methods exist to transport such implants, however, it may be desirable to provide improved apparatuses, systems, and methods for use in holding implants and other device preparation.

SUMMARY

Embodiments of the present disclosure may be directed to apparatuses, systems, and methods for holding prosthetic implants. The systems in certain embodiments may be for use in holding prosthetic implants prior to implantation within a patient's body and prior to coupling to a delivery apparatus used to implant the prosthetic implant within the patient's body. Certain embodiments disclosed herein may relate to apparatuses, systems, and methods for prosthetic implant preparation prior to implantation.

The prosthetic implants in embodiments may comprise implantable prosthetic valves. In embodiments, the implantable prosthetic valves may comprise implantable prosthetic heart valves. The implantable prosthetic heart valves may be configured to replace or repair native aortic, pulmonary, mitral, or tricuspid valves in embodiments. Other forms of implantable prosthetic valves may be utilized in embodiments.

One or more embodiments of the present disclosure include a holder system for an implantable prosthetic valve. The system may include a holder body, and one or more releasable couplers coupled to the holder body and configured to retain the implantable prosthetic valve to the holder body. The system may include an actuator coupled to the holder body and configured to be operated to release the one or more releasable couplers from the implantable prosthetic valve.

One or more embodiments of the present disclosure include a method. The method may include coupling an implantable prosthetic valve to one or more releasable couplers of a holder, the holder including a holder body coupled to the one or more releasable couplers and an actuator coupled to the holder body and configured to be operated to release the one or more releasable couplers from the implantable prosthetic valve.

One or more embodiments of the present disclosure include a method. The method may include operating an actuator of a holder to release an implantable prosthetic valve from one or more releasable couplers of the holder, the holder including a holder body coupled to the one or more releasable couplers and the actuator.

BRIEF DESCRIPTION OF THE DRAWINGS

Features and advantages of the systems, apparatuses, and methods as disclosed herein will become appreciated as the same become better understood with reference to the specification, claims, and appended drawings wherein:

DETAILED DESCRIPTION

Figure 1:
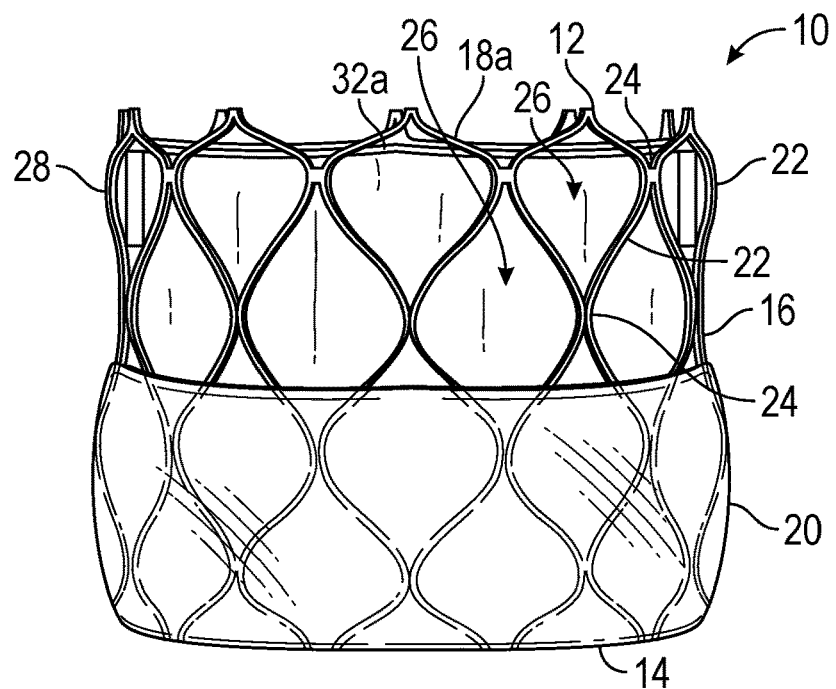
FIG. 1 illustrates a side perspective view of a prosthetic implant according to an embodiment of the present disclosure.

FIG. 1 illustrates a perspective view of a prosthetic implant 10 in the form of an implantable prosthetic valve. The implantable prosthetic valve in embodiments may comprise a replacement heart valve. The prosthetic implant 10 may be configured to be deployed within a portion of a patient's body. The prosthetic implant 10, for example, may be deployed within a native heart valve annulus, which may comprise a native aortic valve, or in embodiments may comprise a native mitral, tricuspid, or pulmonary valve. In embodiments, the prosthetic implant 10 may have other forms, and may comprise a stent or other form of medical implant as desired. The prosthetic implants may be configured to replace or repair a portion of a patient's body.

The prosthetic implant 10 may include a proximal end 12 and a distal end 14, and a length therebetween. The prosthetic implant 10 may include a body in the form of a frame 16. The prosthetic implant 10 may further include one or more of a plurality of leaflets 18a-c coupled to the frame 16 and may include a skirt 20 covering an outer surface of a distal portion of the frame 16.

The frame 16 may comprise a plurality of struts 22 connected at junctures 24. A plurality of openings 26 may be positioned between the struts 22. The openings 26 may be configured to reduce the overall weight of the frame 16, and also allow the frame 16 to be compressed to reduce a diameter of the frame 16 and be expanded to increase a diameter of the frame 16. The frame 16 may be configured to be radially compressed and axially lengthened while being radially compressed. The struts 22 may be configured such that as the frame 16 is compressed to reduce a diameter of the frame 16, the length of the frame 16 may increase. Also, as the frame 16 is expanded to increase the diameter of the frame 16, the length of the frame 16 may decrease. The frame 16 may be compressed in a variety of manners, including use of a crimping device, and may be expanded in a variety of manners, including being expanded with a balloon, being self-expandable, or being mechanically expandable.

The frame 16 may include an outer surface 28 configured to be pressed against interior vasculature of a patient's body. For example, as the frame 16 is expanded, the outer surface 28 may contact and press against the interior vasculature of the patient's body. The outer surface 28 may press against a native annulus, or native leaflets of a heart valve in embodiments. The frame 16 may include an interior surface 30 (marked in FIG. 2) configured to face opposite the outer surface 28 and configured to face towards a flow channel of the implant 10.

The skirt 20 may cover the outer surface 28 of the distal portion of the frame 16 as shown in FIG. 1 and may comprise a membrane or other form of skirt 20. The skirt 20 may improve compliance of the frame 16 with a native valve in which the implant 10 is implanted and may be utilized to couple the leaflets 18a-c to the frame 16 via sutures of another form of coupler.

Figure 2:
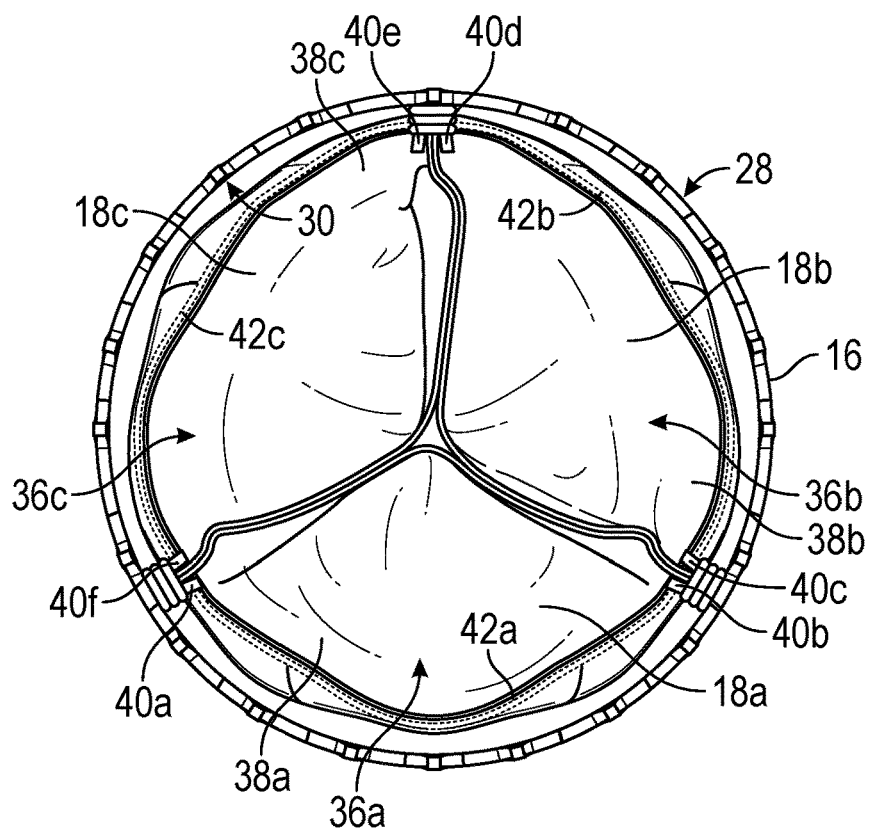
FIG. 2 illustrates a top view of the prosthetic implant shown in FIG. 1 with the leaflets of the implant in a closed position.
Figure 3:
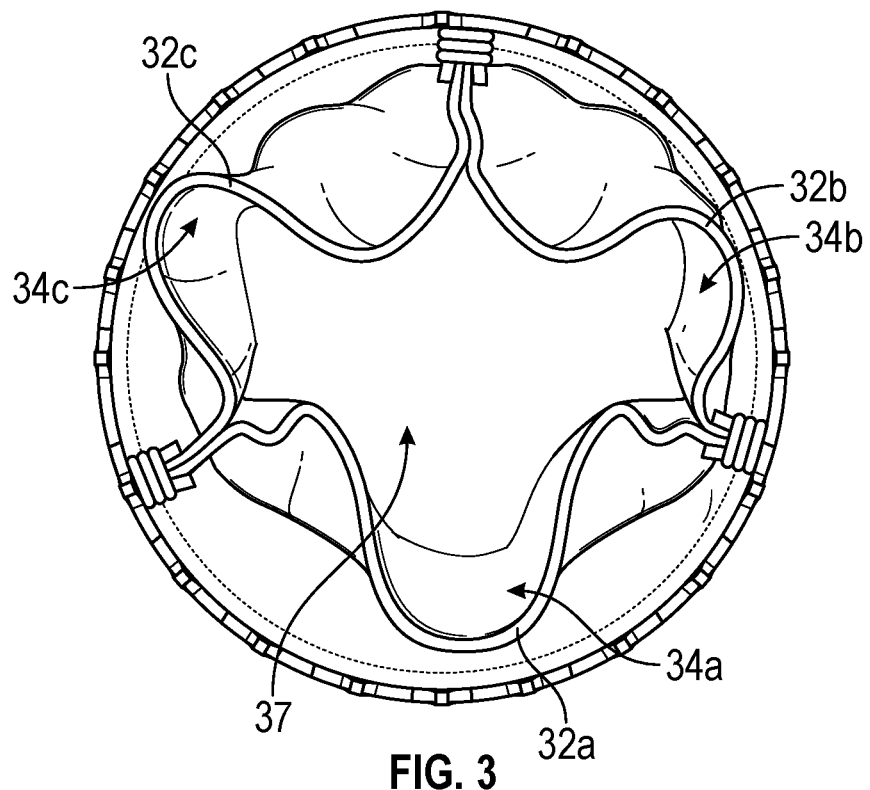
FIG. 3 illustrates a top view of the prosthetic implant shown in FIG. 1 with the leaflets of the implant in an open position.

The plurality of leaflets 18a-c (more clearly shown in FIG. 2) may extend inward from the interior surface 30 of the frame 16. The plurality of leaflets 18a-c may be configured to move towards each other to move to a closed position (as shown in FIG. 2) and be moved away from each other to move to an open position (as shown in FIG. 3). The leaflets 18a-c may each include upper end portions 32a-c (marked in FIG. 3) that are configured to contact each other to close the flow channel of the implant 10 when the leaflets 18a-c are in the closed position. The upper end portions 32a-c are configured to move away from each other to open the flow channel of the implant 10 when the leaflets 18a-c are in the open position. The leaflets 18a-c may move back and forth between open and closed positions or states or configurations to replicate the motion of a native valve.

Each leaflet 18a-c may include an interior surface 34a-c (marked in FIG. 3) configured to face towards the flow channel of the implant 10, and an exterior surface 36a-c (marked in FIG. 2) facing opposite the interior surface 34a-c and facing away from the flow channel 37 of the implant 10. Portions of the interior surface 34a-c of respective leaflets 18a-c may contact each other when the leaflets 18a-c move to the closed position.

Each leaflet 18a-c may include a respective outer portion 38a-c (marked in FIG. 2) that couples to the frame 16 of the implant 10. The coupling may have a variety of forms. For example, each leaflet 18a-c may include tabs 40a-f at the respective outer portion 38a-c of the leaflet 18a-c. The tabs 40a, b may extend from the leaflet 18a, the tabs 40c, d may extend from the leaflet 18b, and the tabs 40e, f may extend from the leaflet 18c. The tabs 40a-f may extend through openings in the frame 16 to couple to the frame 16 and then may be sutured to hold the tabs 40a-f in position. The tabs 40a-f may form commissures of adjacent leaflets 18a-c.

Further, the outer portion 38a-c of each leaflet 18a-c may be sutured to the skirt 20 along a suture line 42a-c. For example, a lower end portion of each leaflet 18a-c opposite the upper end portion 32a-c may be sutured to the skirt 20 at a respective suture line 42a-c. The sutures of the suture line 42a-c may hold the leaflets 18a-c to the frame 16 and prevent undesired fluid flow through the implant 10 outside of the flow channel 37.

The leaflets 18a-c may be configured to open and close during operation such that the proximal end 12 of the implant 10 forms an outflow end of the implant 10, and the distal end 14 of the implant 10 forms an inflow end of the implant 10. The leaflets 18a-c may be configured to impede fluid flow in an opposite direction from the outflow end to the inflow end of the implant 10 when the leaflets 18a-c are in a closed position.

In embodiments, other forms of implants may be utilized, such as stents or other forms of medical devices. The configuration of the implant shown in FIGS. 1-3 may be varied in embodiments.

Figure 4:
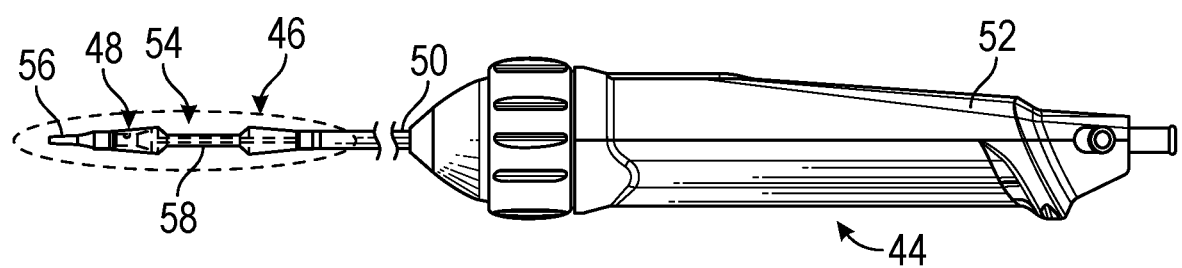
FIG. 4 illustrates a side view of a delivery apparatus according to an embodiment of the present disclosure.

The implant 10 may be configured to be delivered to an implantation site utilizing a delivery apparatus. FIG. 4, for example, illustrates an embodiment of a delivery apparatus 44 that may be utilized to deliver the implant 10 to a desired implantation site. The delivery apparatus 44 may include an elongate shaft 46 having a distal portion 48 and a proximal portion 50. The proximal portion 50 may couple to a housing in the form of a handle 52. The distal portion 48 may include an implant retention area 54 and a distal tip that may include a nose cone 56. The distal portion 48 may further include an inflatable body in the form of a balloon 58. The delivery apparatus 44 may be configured to be positioned within a crimping device to crimp the implant 10 to the implant retention area 54. The elongate shaft 46 may be positioned within the crimping device. The balloon 58 may be configured for the implant 10 to be crimped upon. In embodiments, other forms of deployment mechanisms may be utilized to deploy the implant (e.g., a self expanding implant or a mechanically expandable implant).

Figure 5:
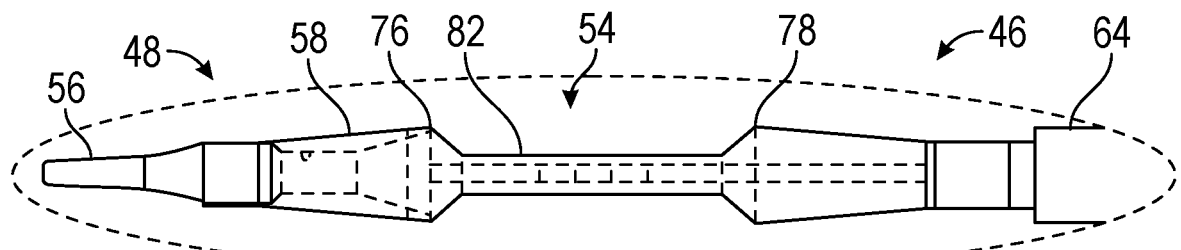
FIG. 5 illustrates a detail view of a portion of a delivery apparatus according to an embodiment of the present disclosure.

FIG. 5 illustrates a close up view of the distal portion 48 of the elongate shaft 46. The implant retention area 54 may be configured for the implant 10 to be crimped over the balloon 58 and positioned in the intermediate portion 82 between a distal shoulder 76 and a proximal shoulder 78 of the balloon 58. In certain embodiments, an outer sheath 64 may be advanced distally to cover the implant 10 positioned within the implant retention area 54 when the implant 10 is crimped. In embodiments, the configuration of the delivery apparatus may be varied from the configuration shown in FIGS. 4 and 5.

Figure 6:
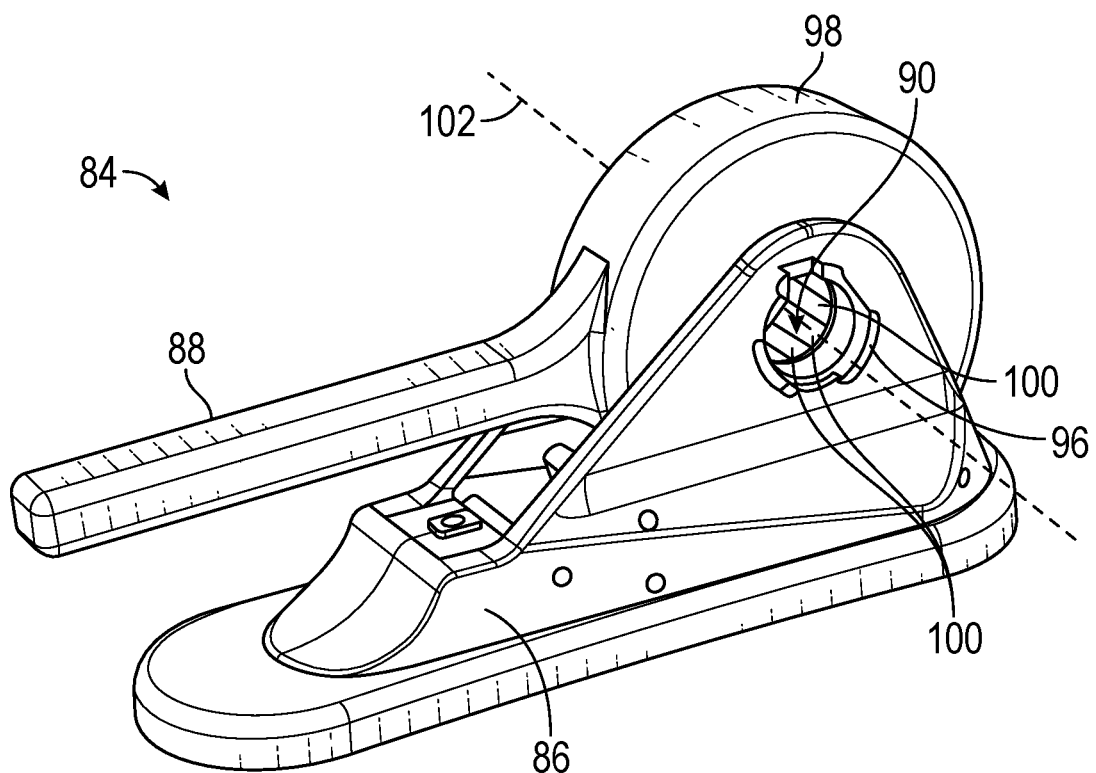
FIG. 6 illustrates a rear perspective view of a crimping device according to an embodiment of the present disclosure.

The implant 10 may be crimped to the implant retention area 54 in a variety of manners. FIG. 6, for example, illustrates a rear perspective view of a crimping device 84 (or a view from the proximal side of the crimping device 84). The crimping device 84 may include a base 86, an actuator in the form of a handle 88, and an opening 96 leading to a channel 90 for the implant 10 and the delivery apparatus 44 to be inserted into. The crimping device 84 may further include a rotatable body 98 configured to be rotated with rotation of the handle 88. The crimping device 84 may operate by a plurality of pressing surfaces 100 surrounding the channel 90 and a central axis 102 and being configured to apply a compressive force to radially compress an implant 10 positioned within the channel 90. An implant 10 positioned within the channel 90 will accordingly be compressed within the channel 90 to the implant retention area 54, due to the radially compressive force of the pressing surfaces 100 against the implant.

Figure 7:
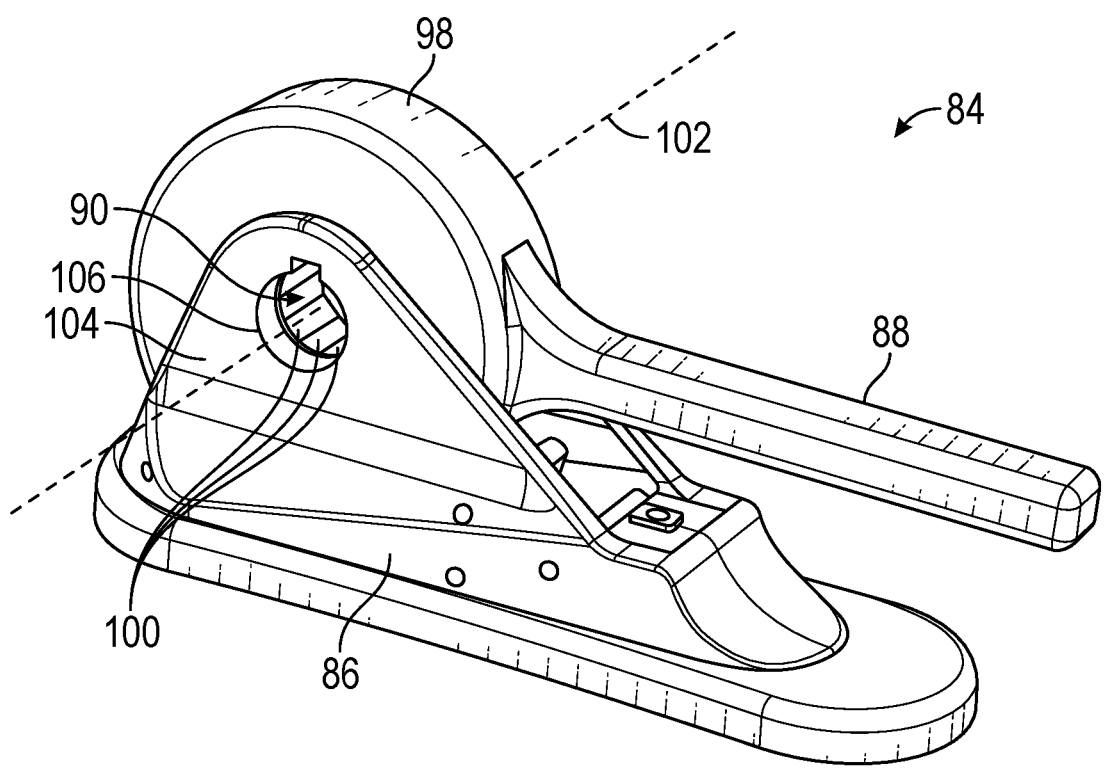
FIG. 7 illustrates a front perspective view of the crimping device shown in FIG. 6.

FIG. 7 illustrates a front perspective view of a crimping device 84 (or a view from the distal side of the crimping device 84). The crimping device 84 may include a distal face 104 including a distal opening 106 that leads into the channel 90. The distal opening 106 may be configured for a portion of the delivery apparatus 44 to pass through upon a crimping operation being performed by the crimping device 84. The configuration of a crimping device may be varied in embodiments as desired.

The implant 10 may be transported prior to being implanted within a patient's body and may be transported prior to a crimping procedure that may be produced by the crimping device 84, to crimp the implant 10 to the delivery apparatus 44. In embodiments, a holder system may be utilized to hold the implant 10 and may be utilized to transport the implant 10. In embodiments, the holder system may be utilized to store the implant 10.

Figure 8:
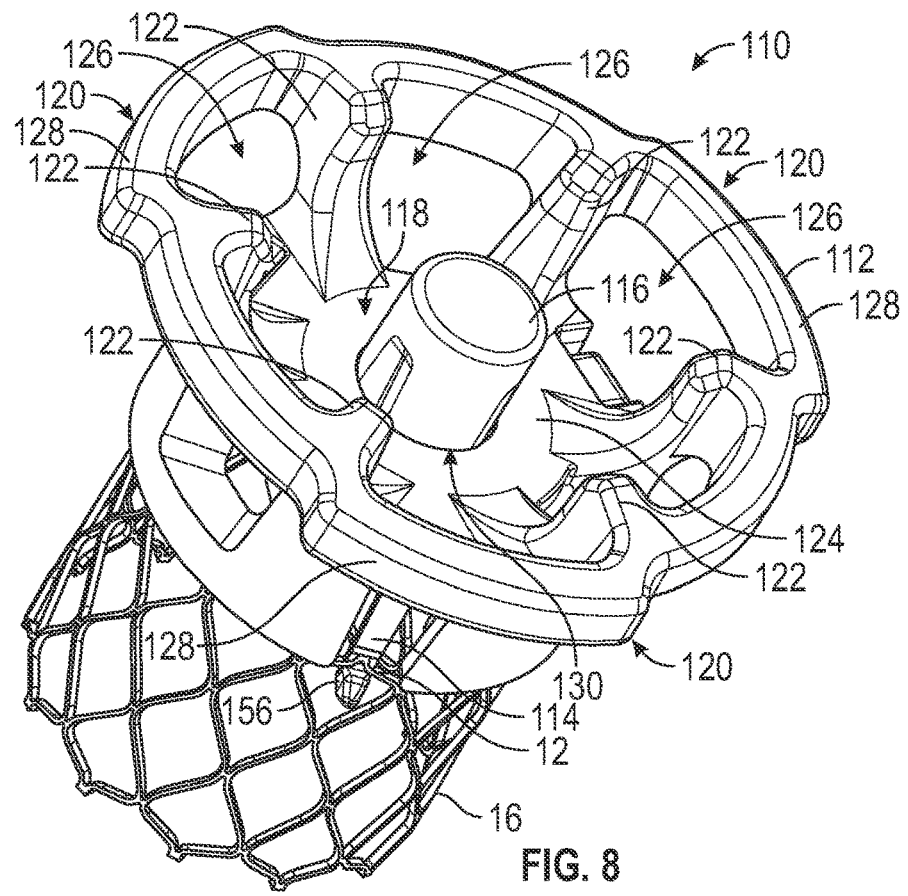
FIG. 8 illustrates a top perspective view of a holder for a prosthetic implant, coupled to a frame of a prosthetic implant according to an embodiment of the present disclosure.

FIG. 8 illustrates an embodiment of a holder 110 that may be utilized in embodiments herein. The holder 110 may include a holder body 112, one or more releasable couplers 114, and an actuator 116. The implant 10 is shown coupled to the holder 110, with only the frame 16 of the implant 10 visible, with features such as the leaflets 18a-c and skirt 20 excluded from view in FIGS. 8, 9, and 15-20 for clarity.

The holder body 112 may include a central portion 118 and one or more grip portions 120 that may extend radially outward from the central portion 118. The grip portions 120 may comprise one or more arms that may extend circumferentially about the central portion 118. For example, as shown in FIG. 8, supports 122 for the grip portions 120 may extend proximally from a proximal surface 124 of the central portion 118. The grip portions 120 may be positioned radially outward of the proximal surface 124 of the central portion 118.

In embodiments, the supports 122 may be in the form of columns as shown in FIG. 8. The proximal portions of the supports 122 may couple to the grip portions 120 and support the grip portions 120 at a distance from the proximal surface 124 of the central portion 118.

The grip portions 120 in the form of arms may extend circumferentially between the supports 122 and may couple the proximal portions of the supports 122 to each other. The grip portions 120 in the form of arms may form a ring extending circumferentially around the central portion 118 and positioned radially outward from the central portion 118.

In embodiments, other forms of one or more grip portions may be utilized.

Figure 10:
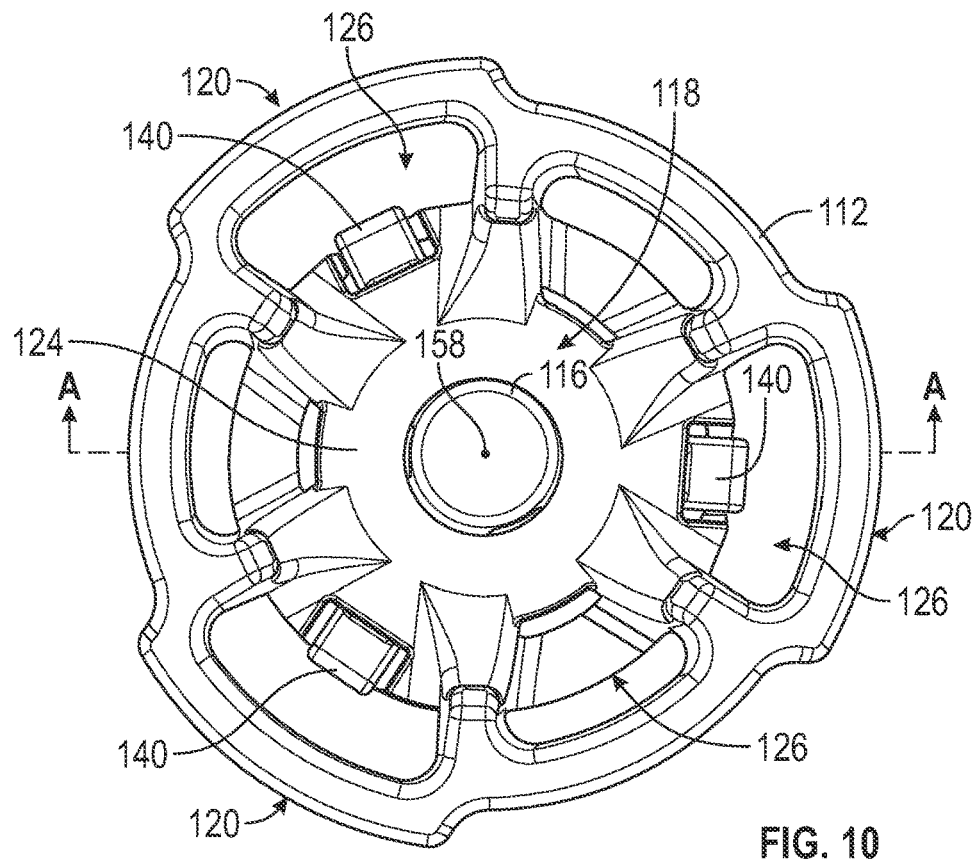
FIG. 10 illustrates a top view of the holder shown in FIG. 8.

Openings 126 may be positioned between the grip portions 120 and the central portion 118, and may be positioned between adjacent supports 122 in embodiments. The openings 126 may extend radially outward from the central portion 118 as shown in FIGS. 8 and 10 and may be sized to allow for grip of the grip portions 120. For example, the grip portions 120 may be configured to be gripped with a hand or a device such as a clamp (such as a hemostat or another form of clamp). The openings 126 may be sized to allow fingers of the hand or a clamp to be positioned around the grip portions 120 to allow for gripping of the holder body 112. The outer surfaces 128 of the grip portions 120 may comprise grip surfaces that are configured for gripping with a hand or a device to hold the holder body 112.

Figure 12:
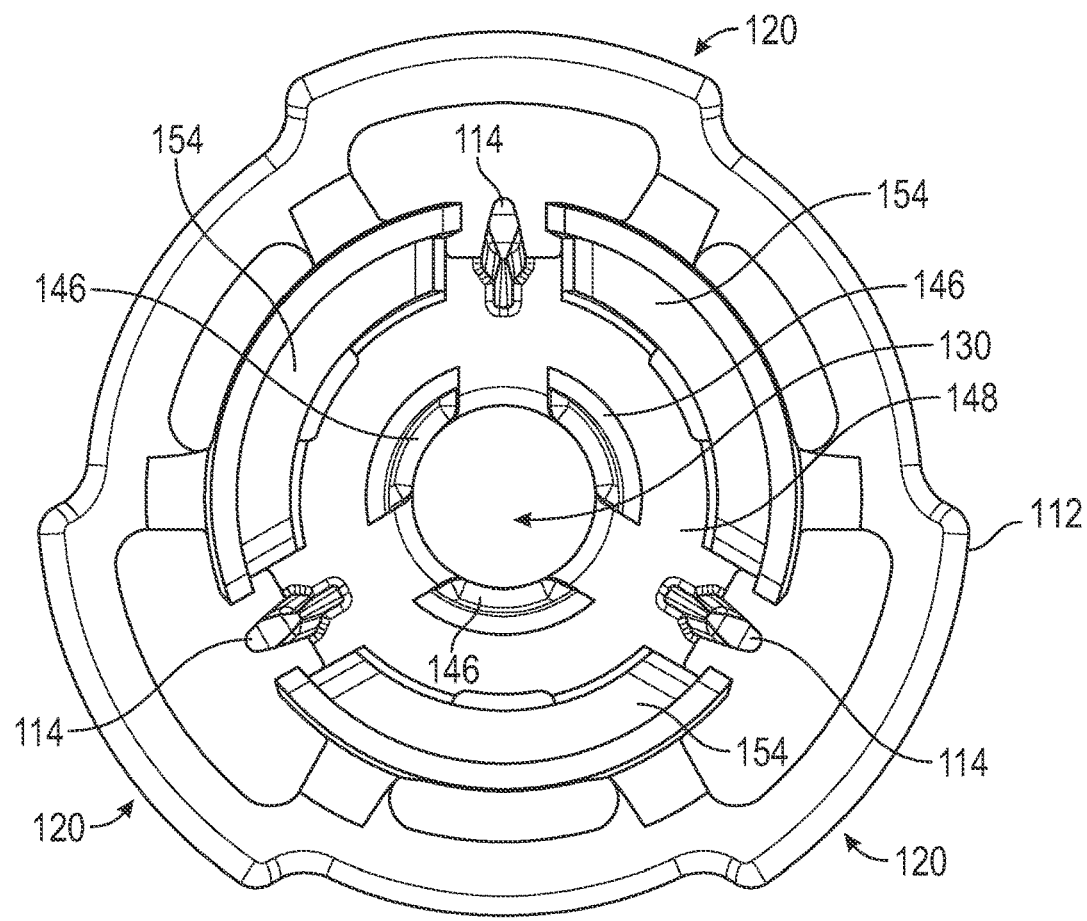
FIG. 12 illustrates a bottom view of the holder body shown in FIG. 8.

The central portion 118 of the holder body 112 may include the proximal surface 124 and may include a central aperture 130 (more clearly shown in FIG. 12). The proximal surface 124 may comprise a flat surface that the supports 122 protrude proximally from. The central aperture 130 may be configured for a portion of the actuator 116 to pass through to be accessed by a user.

Figure 9:
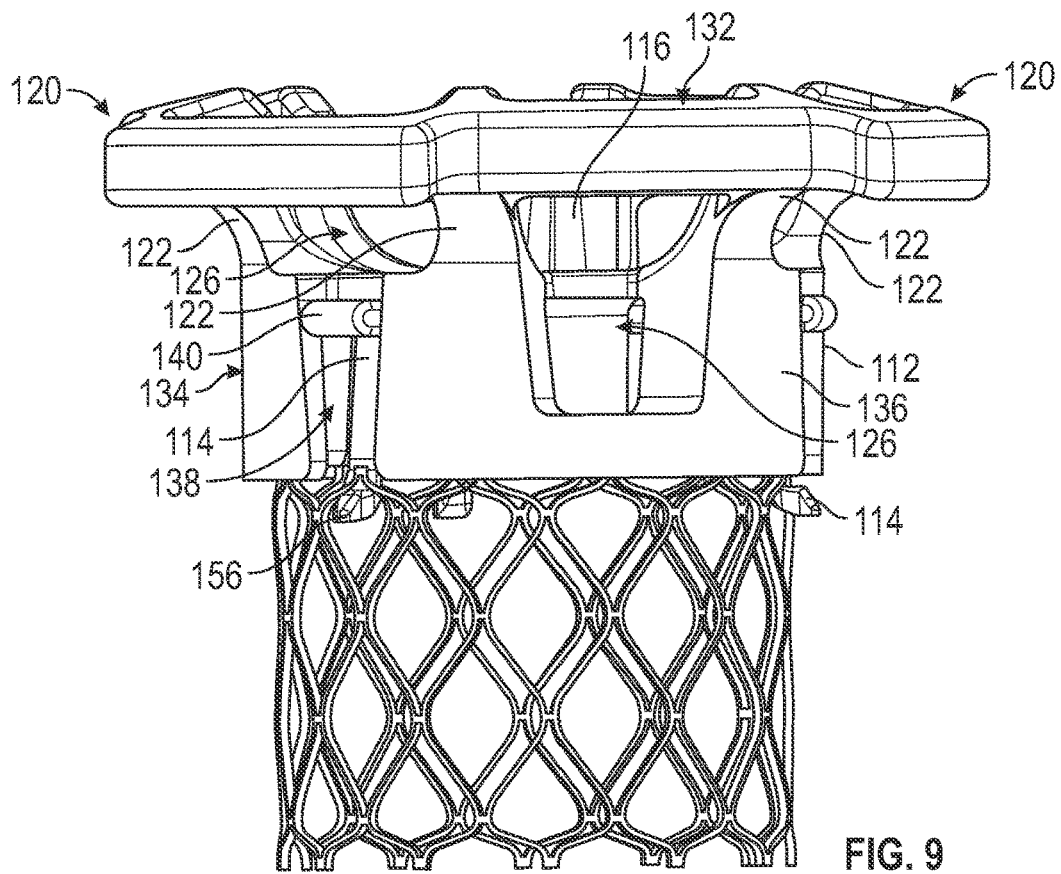
FIG. 9 illustrates a side view of the holder shown in FIG. 8.

Referring to FIG. 9, the holder body 112 may include a proximal portion 132 and a distal portion 134. The proximal portion 132 may include the grip portions 120 and the supports 122 in embodiments. In other embodiments, other features of the holder body 112 may comprise the proximal portion 132 of the holder body 112. The distal portion 134 may be for contacting the implant 10, and may include the central portion 118 in embodiments, although in other embodiments other features of the holder body 112 may comprise the distal portion 134.

The distal portion 134 as shown in FIG. 9 may have a cylindrical shape defined by the outer surface 136 of the holder body 112. The openings 126 may pass through the distal portion 134 to allow for grip of the grip portions 120. The proximal portion 132 and distal portion 134 together may form a "T" shape for the holder body 112 as shown in FIG. 9, although in embodiments another shape, such as an entirely cylindrical shape, or other shape (e.g., triangular, square, oval, etc.) may be utilized as desired. In an embodiment in which a "T" shape is utilized, with the grip portions 120 extending radially outward from the distal portion 134 as shown in FIG. 9, a user may more easily grip the grip portions 120 to hold the holder body 112 and operate the actuator 116.

The distal portion 134 may include one or more channels 138 in the outer surface 136 that may allow arms 140 of the actuator 116 to pass through. The channels 138 may be utilized to guide the arms 140 of the actuator 116 to reduce the possibility of rotation of the actuator 116 upon a sliding movement of the actuator 116.

FIG. 10 illustrates a top view of the holder body 112. The grip portions 120 are shown to extend radially outward from the central portion 118.

Figure 11:
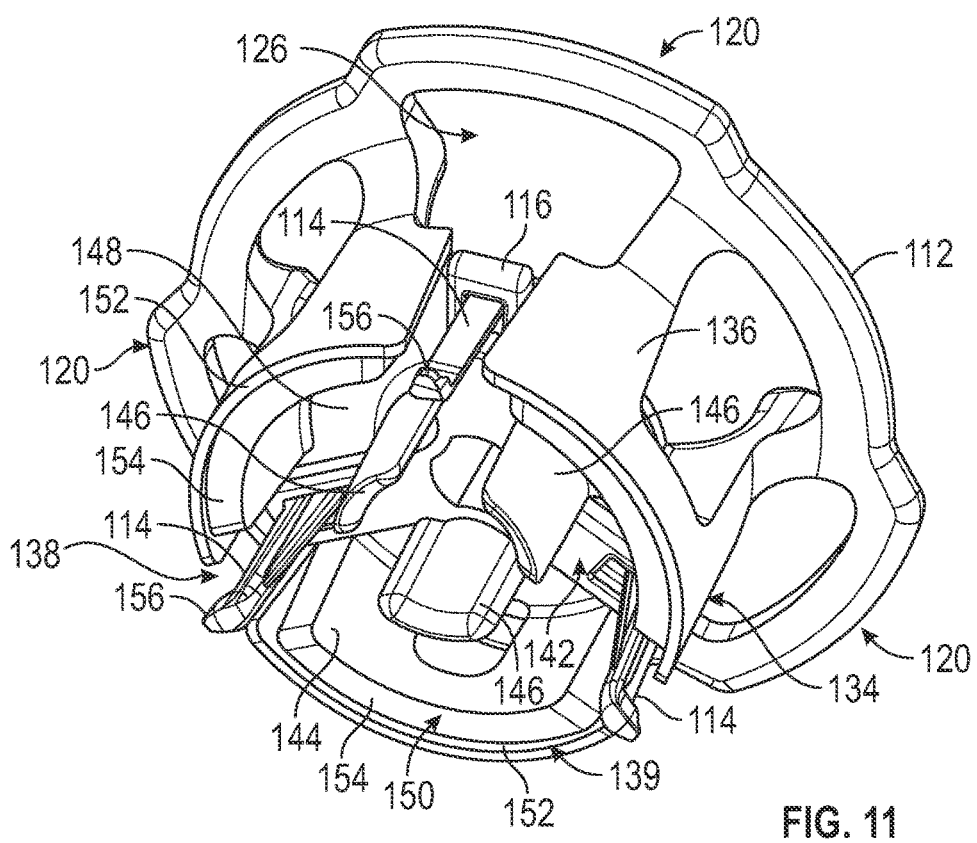
FIG. 11 illustrates a bottom perspective view of the holder shown in FIG. 8, with the prosthetic device excluded from view.

FIG. 11 illustrates a bottom perspective view of the holder body 112 with the implant 16 excluded from view. The distal portion 134 of the holder body 112 is shown to include a central cavity 142 for receiving the actuator 116. The central cavity 142 may be defined by an interior surface 144 of the holder body 112 that faces opposite the outer surface 136 and that faces the central cavity 142. One or more guide supports 146 may be positioned within the central cavity 142 and may extend distally from a central surface 148 of the holder body 112 that faces opposite the proximal surface 124 shown in FIG. 8. The guide supports 146 may be positioned between the arms 140 of the actuator 116 and may be configured to guide the arms 140 of the actuator 116 to reduce the possibility of rotation of the actuator 116 upon a sliding movement of the actuator 116. The guide supports 146 may have an arc shape as shown in FIG. 11, or may have another shape as desired. The arms 140 of the actuator 116 may slide between the guide supports 146.

The distal portion 134 of the holder body 112 may include a receiving portion 139 that is configured to receive the implant 10, and particularly an end 12 of the implant 10. The end 12 may be a proximal end that is opposite the skirt 20 as shown in FIG. 1 and proximal of the upper end portions 32a-c of the leaflets 18a-c. The implant 10 may be positioned within the receiving portion 139 such that the implant 10 extends axially with respect to the holder 110 and in a distal direction relative to the holder 110.

The receiving portion 139 may comprise a recess 150 for receiving a portion of the implant 10. The recess 150 may be defined by a lip 152 that extends circumferentially about the holder body 112 and a contact surface 154 that faces distally. The lip 152 may extend distally from the contact surface 154 and may be configured to reduce the possibility of the implant 10 slipping or otherwise moving with respect to the holder body 112 when coupled to the holder body 112.

The contact surface 154 may be configured for contacting a portion of the implant 10, which may be a proximal end 12 of the implant. The contact surface 154 may support the implant 10 upon the implant 10 being coupled to the one or more releasable couplers 114.

FIG. 12 illustrates a bottom view of the holder body 112, with the actuator 116 excluded from view.

Various other configurations of holder bodies may be utilized in embodiments as desired. For example, certain features of the holder body 112 may be excluded, added to, or may have features substituted with other features as desired.

Referring to FIG. 11, the one or more releasable couplers 114 may be coupled to the holder body 112 and may be configured to retain the implant 10 to the holder body 112. The one or more releasable couplers 114 may include elongate arms as shown in FIG. 11 that may extend distally from the central surface 148. The releasable couplers 114 may extend along the channels 138 of the holder body 112 as shown in FIG. 11 for example. The one or more releasable couplers 114 may extend in a distal direction to engage the implant 10. The one or more releasable couplers 114 may include hooks 156 at distal portions of the elongate arms that are configured to engage a frame of the implant 10. The hooks 156 may protrude radially outward as shown in FIG. 11, or another direction of protrusion may be utilized in embodiments. Hooks 156 engaging the frame of the implant 10 is shown in FIGS. 8 and 9 for example. The portion of the implant 10 at the proximal end 12 (as shown in FIG. 1 for example) may include an exposed (or uncovered) frame 16 that allows the hooks 156 to pass into the openings 26 between the struts 22 to engage the frame 16. In embodiments, other configurations of releasable couplers may be utilized as desired.

The one or more releasable couplers 114 may include a plurality of releasable couplers 114 that are circumferentially spaced from each other as shown in FIG. 11, or other spacings may be utilized as desired. The one or more releasable couplers 114 may be positioned at the receiving portion 139 of the holder body 112, and circumferentially spaced at the receiving portion 139. Two or more, or three or more releasable couplers, or another number may be utilized as desired. Three releasable couplers 114 are shown in FIG. 11, although another number may be utilized in embodiments.

Figure 15:
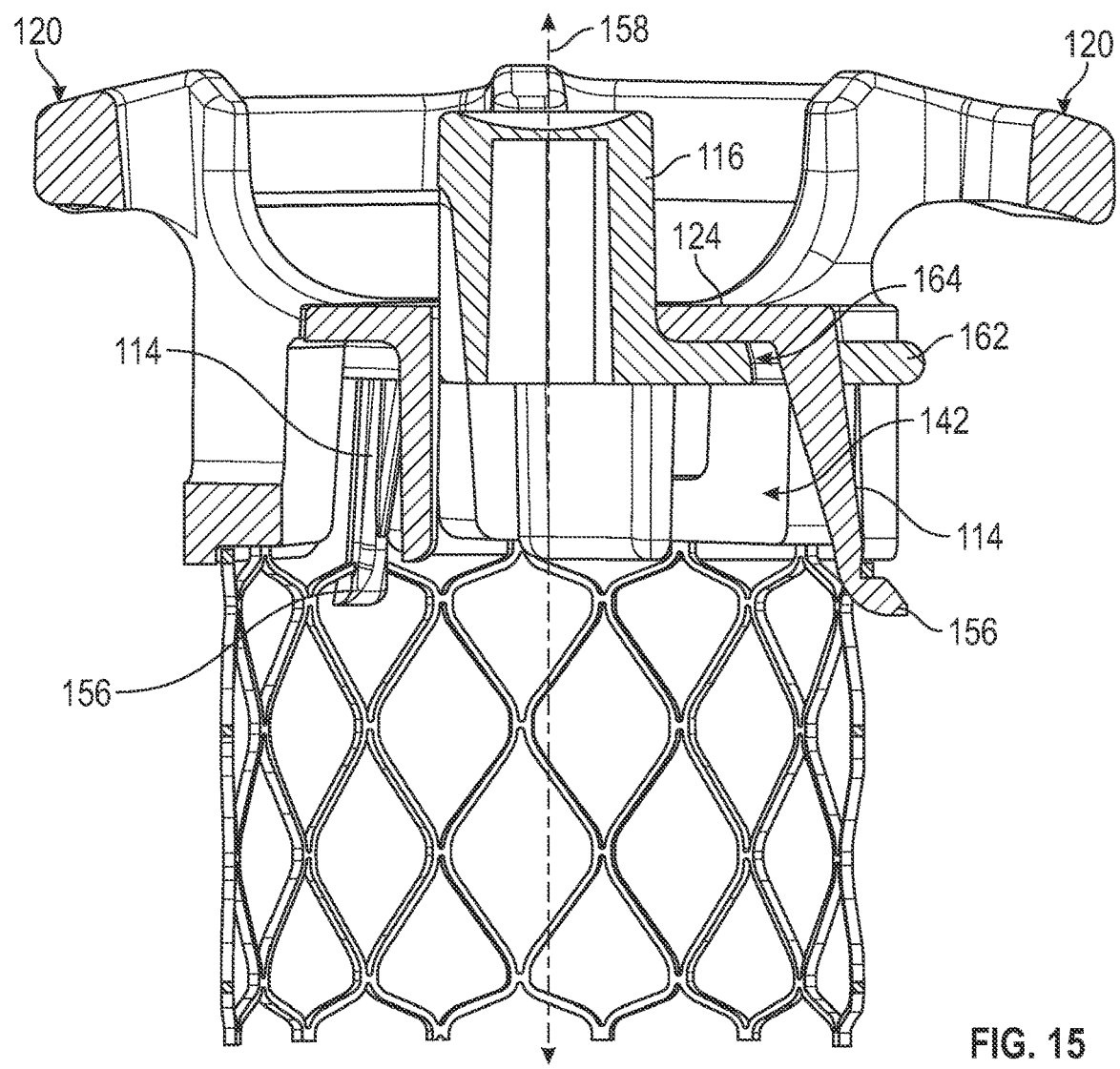
FIG. 15 illustrates a cross sectional view of the holder and prosthetic implant along line A-A shown in FIG. 10.

The one or more releasable couplers 114 may be angled radially outward as shown in the cross sectional view of FIG. 15 for example. Referring to FIG. 15, the one or more releasable couplers 114 may be angled radially outward relative to a central axis 158 of the holder. As such, as the releasable couplers 114 extend distally, the outer radial extent of the releasable couplers 114 increases. The releasable couplers 114 may be configured to be deflected radially inward, to allow the hooks 156 to deflect radially inward and release from the frame of the implant 10. The releasable couplers 114 may be configured to be deflected via the operation of the actuator 116.

Figure 13:
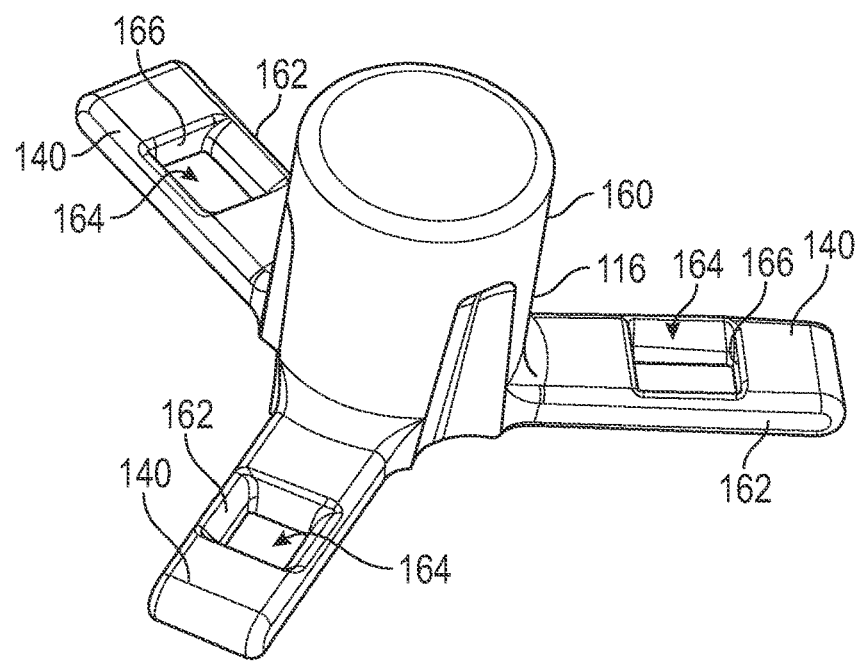
FIG. 13 illustrates a top perspective view of the actuator shown in FIG. 8.

Referring to FIG. 13, the actuator 116 is shown separate from the holder body 112. The actuator 116 in embodiments may be coupled to the holder body 112 and configured to be operated to release the one or more releasable couplers 114 from the implant 10. As shown in FIG. 13, the actuator 116 may include a central portion 160 and radially extending portions 162 that extend radially outward from the central portion 160. Three radially extending portions 162 are shown in FIG. 13, although a greater or lesser number may be utilized in embodiments as desired. The number of radially extending portions 162 may correspond to the number of releasable couplers 114 in embodiments.

The central portion 160 may comprise a central column in the form of a button as shown in FIG. 13. The button may be configured to pass through the central aperture 130 marked in FIG. 12 and may be accessible at the proximal side of the holder body 112 as shown in FIG. 8. In embodiments, other configurations of central portions 160 may be utilized as desired.

The radially extending portions 162 may comprise arms as shown in FIG. 13 and may be spaced circumferentially from each other. The spacings of the arms may correspond to the positions of the releasable couplers 114 in embodiments. Each arm may include an opening 164 that a respective releasable coupler 114 may be configured to pass through. For example, an elongate arm of the respective releasable coupler 114 may pass through the opening 164 and may be configured to slide within the opening 164.

The radially extending portions 162 may each include a deflection surface 166 that may be configured to press against the releasable couplers 114 as the actuator 116 is moved. In embodiments, the actuator 116 may include one or more deflection surfaces 166.

Figure 14:
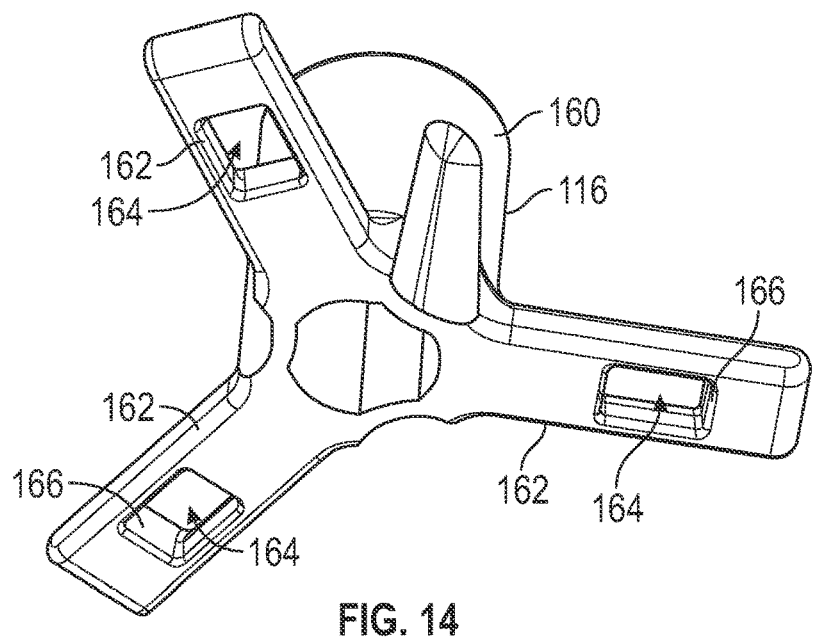
FIG. 14 illustrates a bottom perspective view of the actuator shown in FIG. 8.

FIG. 14 illustrates a bottom perspective view of the actuator 116.

Referring to FIGS. 11 and 15, the actuator 116 may be positioned within the central cavity 142 of the holder body 112 with the releasable couplers 114 passing through the openings 164 shown in FIG. 14. The actuator 116 may be configured to be moved to release the one or more releasable couplers 114 from the implant 10. For example, the actuator 116 may be configured to slide within the central cavity 142 distally to release the one or more releasable couplers 114 from the implant 10. The actuator 116 may be slid to deflect the one or more releasable couplers 114 from the implant 10 to release the one or more releasable couplers 114 from the implant 10.

Referring to FIG. 15, with the implant 10 engaged with the releasable couplers 114, the actuator 116 may be in a proximal position with the button raised above the proximal surface 124. The radially extending portions 162 of the actuator 116 may be in a raised proximal position as well. The releasable couplers 114 deflect radially outward to engage the frame of the implant 10.

Figure 16:
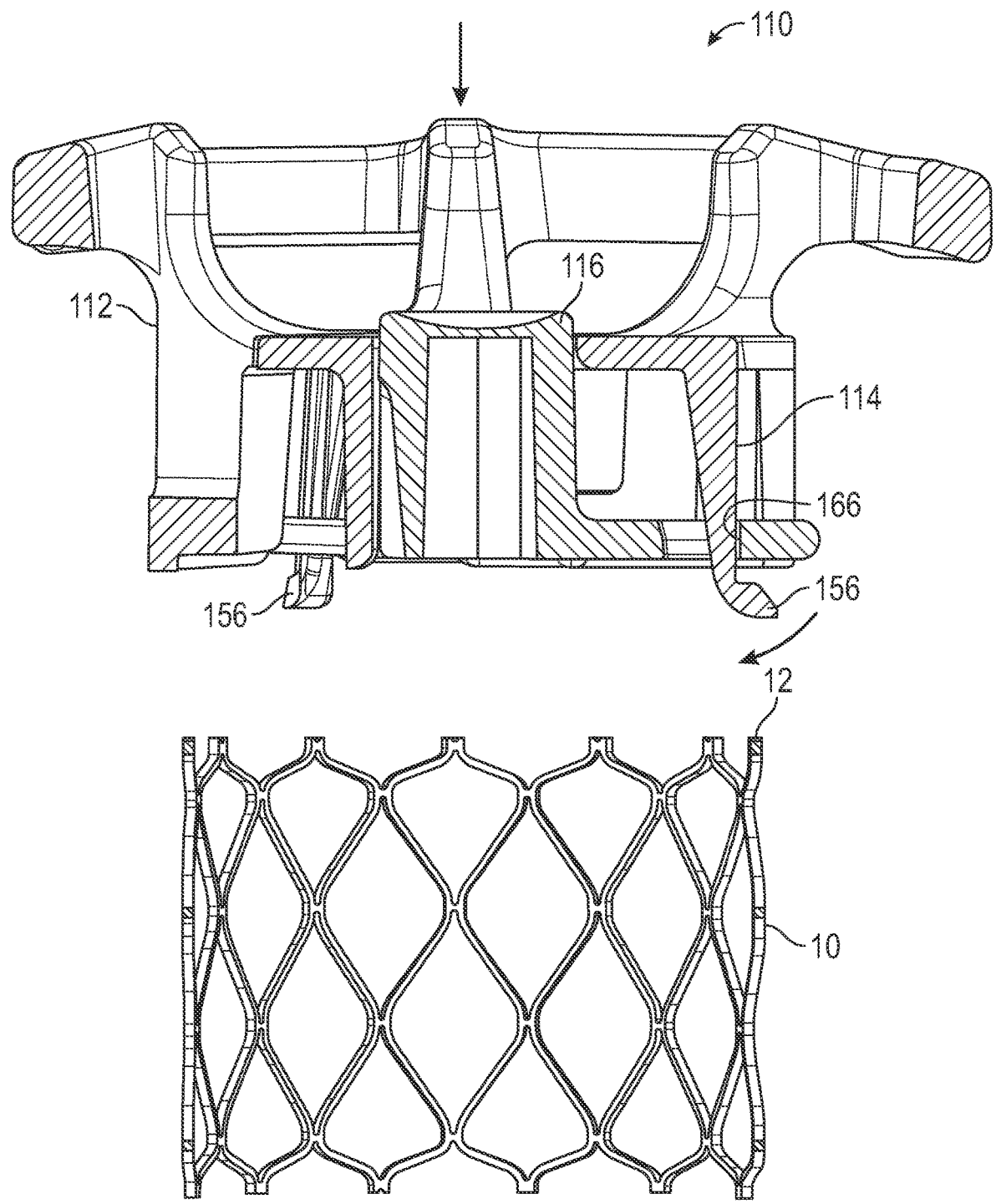
FIG. 16 illustrates a cross sectional view of the holder and prosthetic implant along line A-A shown in FIG. 10, with the actuator moved from the position shown in FIG. 15.

Referring to FIG. 16, upon the actuator 116 being operated by being pressed in a distal direction relative to the holder body 112, the deflection surfaces 166 may be slid relative to the releasable couplers 114 to deflect the releasable couplers 114 from the implant 10 to release the releasable couplers 114 from the implant 10. The button of the actuator 116, for example, may be pressed in a distal direction relative to the holder body 112 to slide the deflection surfaces 166 relative to the releasable couplers 114 to deflect the releasable couplers 114 from the implant 10 to release the releasable couplers 114 from the implant 10. The deflection surfaces 166 may press against the distal portions of the releasable couplers 114 to move the distal portions radially inward and move the hooks 156 radially inward. The hooks 156 may move radially inward to disengage from the frame of the implant 10 and allow the implant 10 to move distally away from the holder 110.

The implant 10, released from the holder 110, may then be utilized for implantation within a patient's body, and utilized in a preparation process such as crimping of the implant 10 to a delivery apparatus.

With the holder 110 coupled to the implant 10, the holder 110 may be positioned at an end 12 of the implant 10, with the central axis 158 of the holder 110 aligned with a central axis of the implant 10. The implant 10 may extend axially from the holder 110 and in a distal direction relative to the holder 110. The holder 110, as shown in FIGS. 8, 9, and 15, for example, may be positioned to cap the end 12 of the implant 10, with the implant 10 extending longitudinally away from the holder 110 in a distal direction. The holder 110 may cover the end 12 of the implant 10 and the holder 110 (particularly the grip portions 120) may extend radially outward from implant 10.

The holder 110 may hold an end 12 of the implant 10 to allow the remainder of the implant 10 extending longitudinally away from the holder 110 to be uncovered by the holder 110. Such a feature may enhance the ability of the implant 10 to be sterilized while coupled to the holder 110, as the holder 110 may be positioned to allow sterilizing gas or another sterilizing substance to contact the implant 10. For example, the holder 110 may be positioned at an end 12 of the implant 10 to allow the implant 10 to be suspended within a container that may be utilized for sterilization of the implant. The holder 110 may be positioned at the end 12 of the implant 10 to allow the portions of the implant 10 extending longitudinally away from the holder 110 to be uncovered by the holder 110 and exposed, to allow sterilizing gas or another sterilizing substance to contact these uncovered portions of the implant 10.

Figure 17:
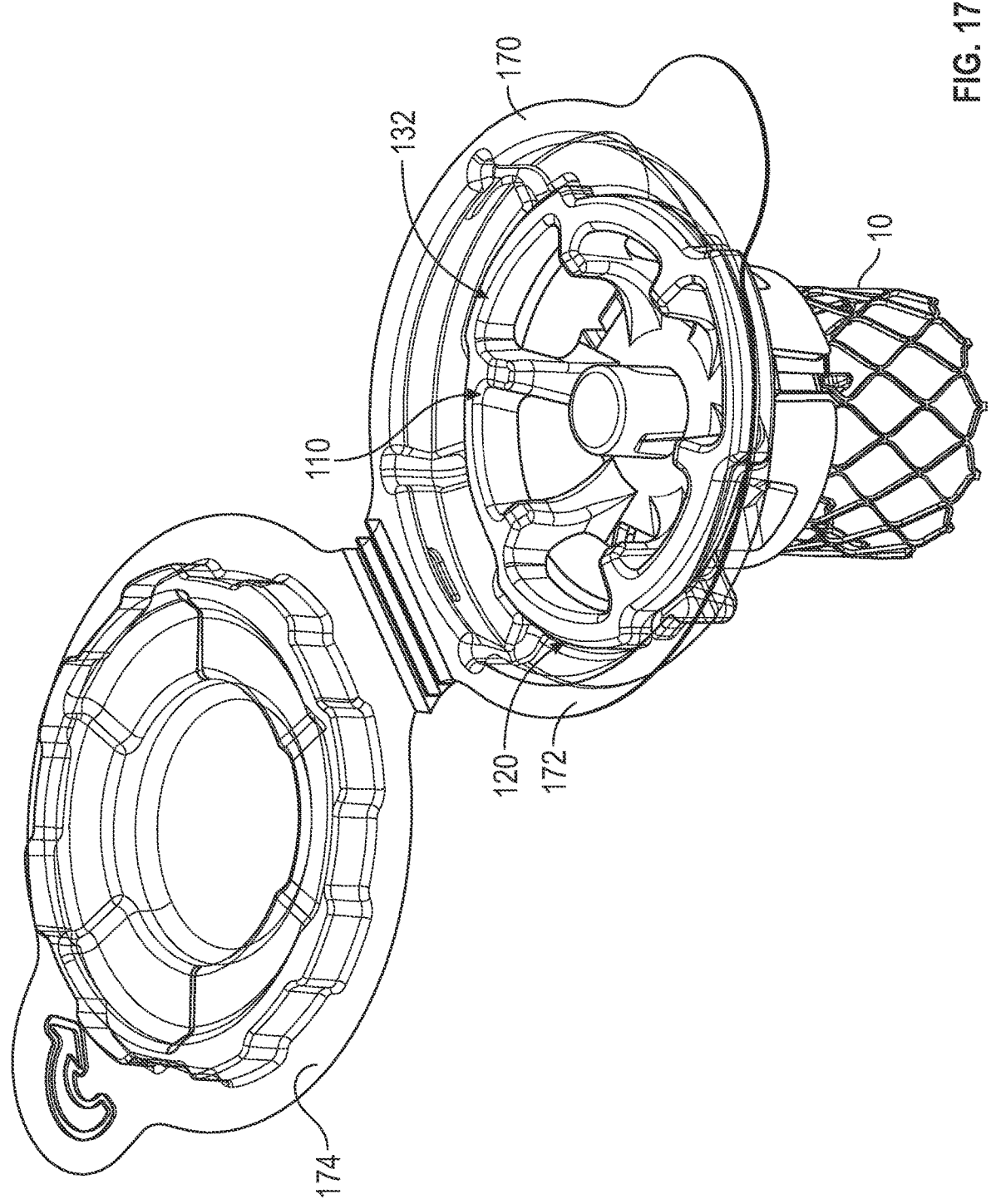
FIG. 17 illustrates a perspective view of the holder shown in FIG. 8 coupled to a retainer.

FIG. 17, for example, illustrates the proximal portion 132 of the holder 110 that may couple to a retainer 170 that may be utilized to support the holder 110. The retainer 170 may include a ring 172 and a lid 174 coupled to the ring 172. The ring 172 may be configured to extend around the proximal portion 132 of the holder 110 and may have a shape that fits the shape of the proximal portion 132 of the holder 110, including the shape of the grip portions 120. The lid 174 may be pivotally coupled to the ring 172 and may be configured to form a friction fit with the ring 172 when closed over the holder 110. The retainer 170 may leave the distal portion of the holder 110 uncovered, and may leave the implant 10 uncovered, to allow sterilizing gas or another sterilizing substance to contact these uncovered portions of the implant 10.

Figure 18:
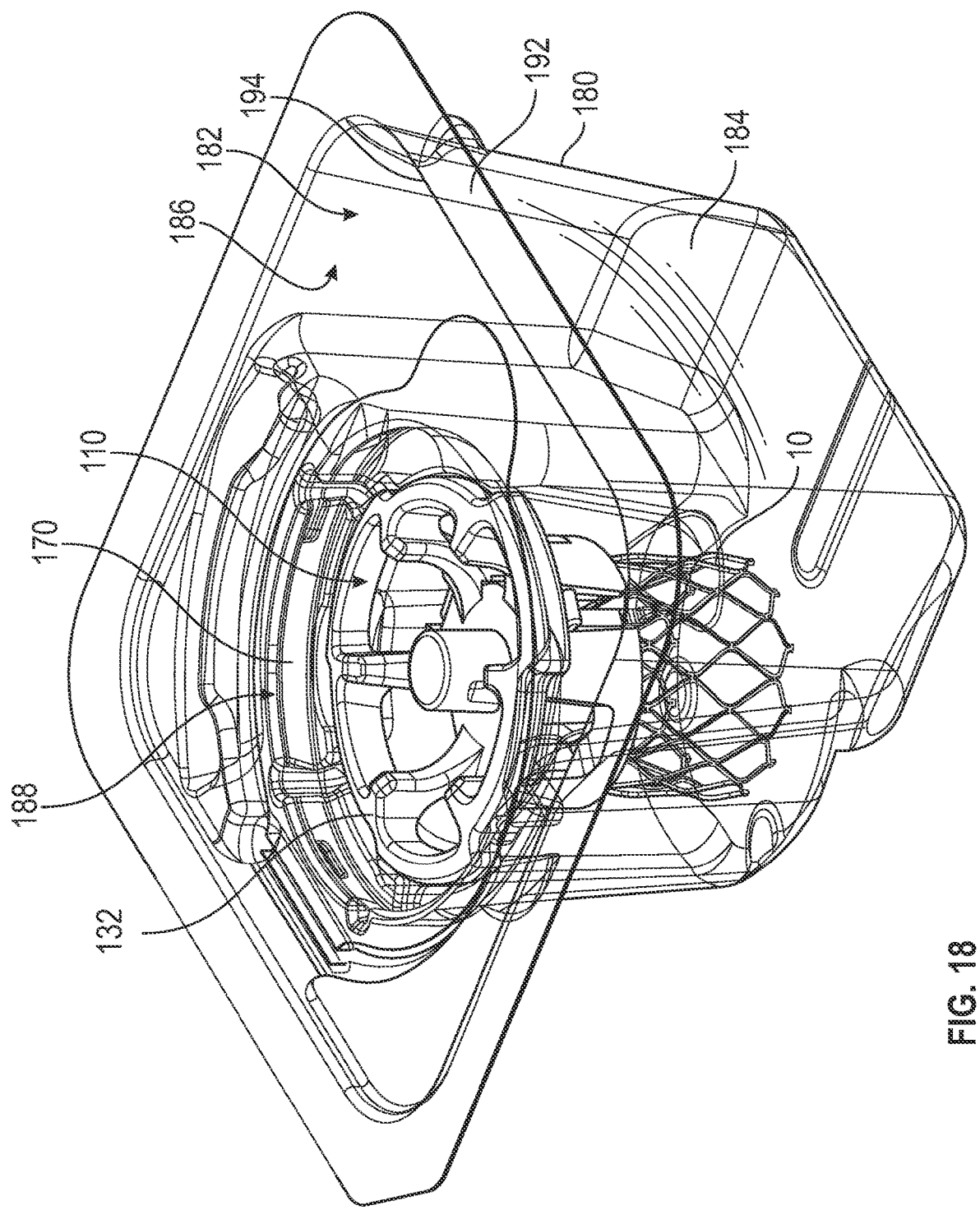
FIG. 18 illustrates a perspective view of the holder, retainer, and prosthetic implant shown in FIG. 17 positioned within a container.

The retainer 170 may be utilized to support the holder 110 for insertion and removal from a container 180 as shown in FIG. 18 for example. FIG. 18 illustrates that the holder 110, the implant 10, and the retainer 170 may be fit into a container 180 that may be utilized to transport, store, and sterilize the implant 10. The lid 174 is excluded from view in FIG. 18 for clarity, but may be closed over the ring 172 and the holder 110 as desired.

The container 180 may be configured to retain the holder body 112 of the holder 110 and the implant 10 coupled to the releasable couplers 114. The container 180 as shown in FIG. 18 may include a cavity 182 and one or more walls 184 having interior surfaces 186 that define the cavity 182. The holder body 112 is configured to couple to the container 180 such that the holder body 112 suspends the implant 10 within the cavity 182. For example, the proximal portion 132 of the holder body 112 may be coupled to the retainer 170, which may fit into a recess 188 of the container 180 that is shaped to receive the retainer 170. In embodiments, the retainer 170 may be excluded and the holder body 112 may be configured to directly contact the recess 188 of the container 180. In embodiments, as shown in FIG. 19, a lid 190 may be coupled to an upper surface 192 of the container 180 and may cover an upper opening 194 of the container 180.

Figure 19:
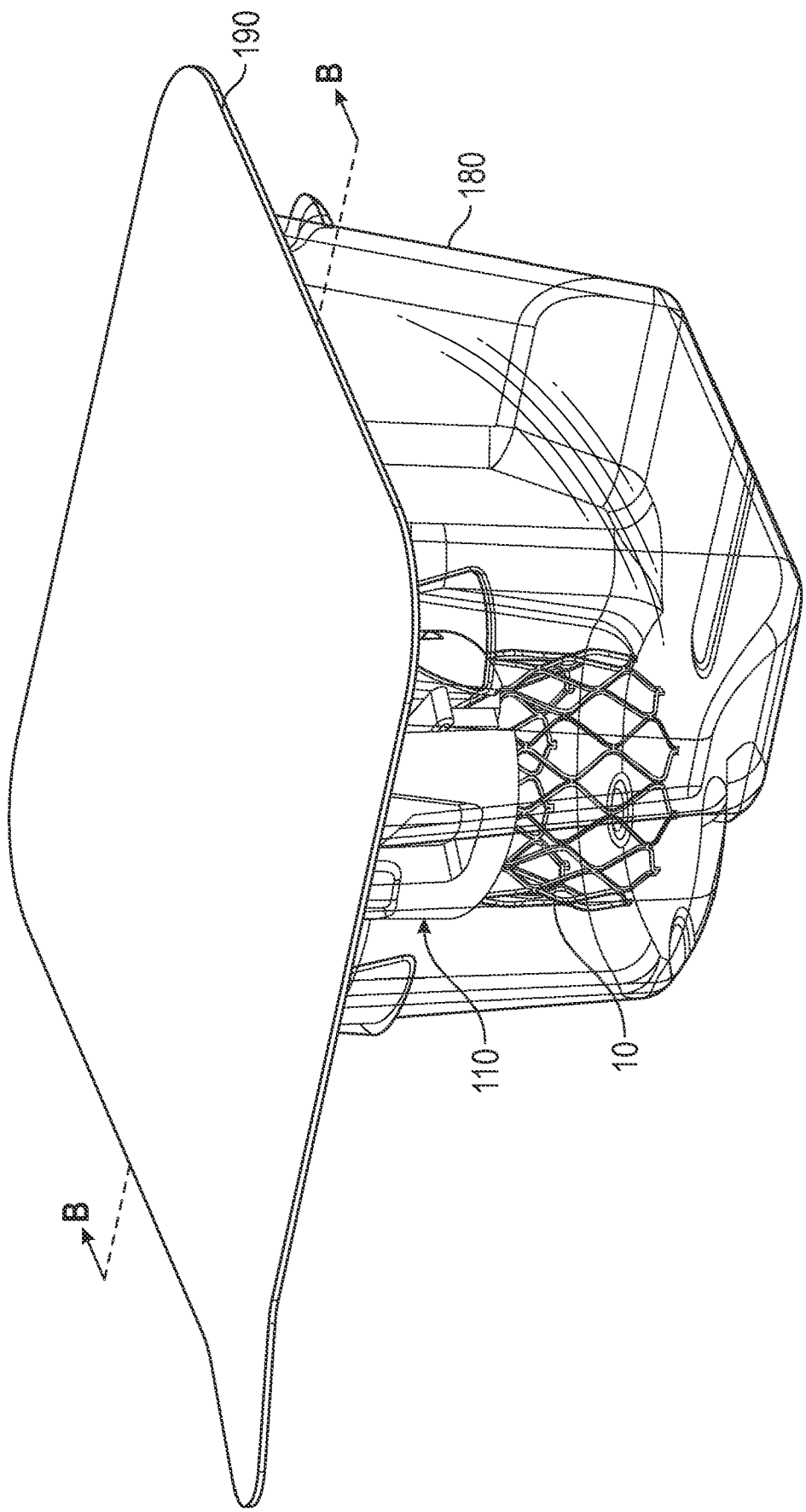
FIG. 19 illustrates a perspective view of a lid coupled to the container shown in FIG. 18.
Figure 20:
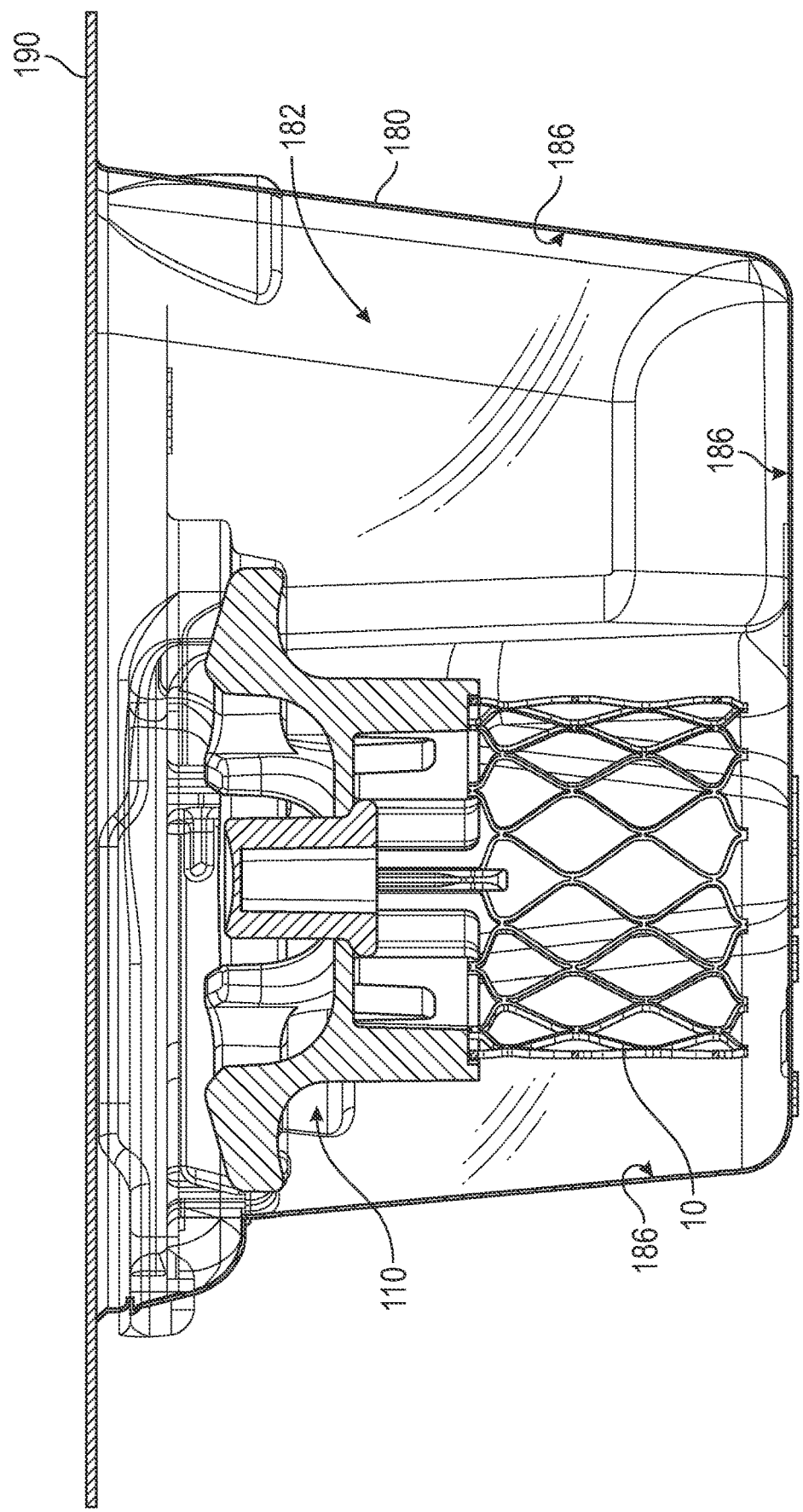
FIG. 20 illustrates a cross sectional view of the holder, retainer, and prosthetic implant positioned within the container shown in FIG. 18, along line B-B shown in FIG. 19.

FIG. 20 illustrates a cross sectional view of the holder 110 coupled to implant 10 and positioned within the container 180, along line B-B in FIG. 19. The holder 110 and implant 10 may be in the configuration shown in FIG. 18. The holder 110 may suspend the implant 10 within the container 180 such that the implant 10 does not contact the interior surfaces 186 of the container 180. Such a feature may beneficially allow the implant 10 to be sterilized within the container 180 without the implant 10 being in contact with a portion of the container 180, which may block a sterilizing gas or other substance from contacting the implant 10. Features of the implant 10 shown in FIGS. 1-3 such as the prosthetic valve leaflets 18a-c and the skirt 20, which may be considered to be "soft" components of the implant 10 are not in contact with any surface, including a surface of the holder 110. As such, the "soft" components may be entirely uncontacted by the holder 110 and the container 180 during sterilization, to improve sterilization of these components.

The lid 190, in embodiments, may be a gas permeable lid 190 that may allow sterilizing gas such as ethylene oxide, or anther sterilizing gas, to permeate through the lid 190 and into the cavity 182 of the container 180. The gas permeable lid 190 may cover the cavity 182 and may seal the cavity 182. As such, the implant 10 may be sterilized within the container 180 with the lid 190 sealing the cavity 182. In embodiments, other forms of sterilization may be utilized.

In operation, upon fabrication of the implant 10, the implant 10 may be coupled to the holder 110. The implant 10 may be coupled to one or more releasable couplers 114 of the holder 110, with the holder 110 including the holder body 112 coupled to the one or more releasable couplers 114 and an actuator 116 coupled to the holder body 112 and configured to be operated to release the one or more releasable couplers 114 from the implant 10. An end 12 of the implant 10, and preferably the proximal end 12 as shown in FIG. 1, may be positioned within the receiving portion of the holder 110 and engaged with the releasable couplers 114. The end 12 of the implant 10 may be contacted to the contact surface 154 of the holder body 112. The releasable couplers 114 may engage a frame of the implant 10. The implant 10 may be positioned as shown in FIG. 9, for example.

The holder 110 coupled to the implant 10 may then be coupled to the retainer 170 as shown in FIG. 17. The lid 174 of the retainer 170 may be closed over the ring 172. The holder 110, implant 10, and retainer 170 may then be inserted into the container 180, in a position as shown in FIG. 18. The implant 10 coupled to the releasable couplers 114 may be positioned within the container 180. The lid 190 as shown in FIG. 19 may be placed over the upper surface 192 of the container 180 (marked in FIG. 18) to cover and seal the cavity 182 of the container 180. The lid 190 may be applied over the cavity 182 of the container 180 with the implant 10 coupled to the releasable couplers 114 within the container 180. The lid 190 may be a gas permeable lid that covers the cavity 182.

The implant 10 may be suspended within the cavity 182 of the container 180 such that the prosthetic valve leaflets 18a-c of the implant 10 do not contact a wall of the container 180. The implant 10 may be suspended within the cavity 182 of the container 180 such that the skirt 20 of the implant 10 does not contact a wall of the container 180.

With the holder 110, retainer 170, and implant 10 positioned within the sealed container 180, the implant 10 may be sterilized. For example, a sterilized gas may be passed into the cavity 182 of the container 180 to sterilize the implant 10 therein. The sterilized gas may pass through the gas permeable lid 190. The implant 10 may be sterilized within the container 180 with the lid 190 applied over the cavity 182 of the container 180. In embodiments, with the holder 110, retainer 170, and implant 10 positioned within the sealed container 180, the implant 10 may be transported to be sterilized. For example, the holder 110, retainer 170, and implant 10 positioned within the sealed container 180 may be transported to a sterilization facility, and the holder 110 may be utilized to support and secure the implant 10 during such transportation.

Following sterilization, the container 180 may be placed within another container, such as a sealed bag or the like. The implant 10 may be stored for a duration, and retained by the holder 110 during such storage.

Following sterilization, and possibly during a device preparation procedure, the holder 110, retainer 170, and implant 10 may be transported to a device preparation area, such as a clinician's preparation area, such as the preparation area that may be utilized by a surgeon. The holder 110 may be utilized to support and secure the implant 10 during such transportation.

The lid 190 may be removed from the container 180. The retainer 170 may then be grasped and removed from the container 180 with the holder 110 and the implant 10 coupled thereto. The retainer 170 may then be removed from the holder 110 and the implant 10. The implant 10 coupled to the releasable couplers 114 may be removed from the container 180 in which the implant 10 was sterilized.

The implant 10 coupled to the holder 110 may be positioned proximate a container such as a container that may include a fluid for moisturizing the implant 10. The implant 10 and holder 110 may be positioned over such a container. A user may grip the grip portions 120 shown in FIG. 15. The user may then operate the actuator 116 of the holder 110 to release the implant 10 from the releasable couplers 114 of the holder 110 as shown in FIG. 16. The actuator 116 may be moved to release the releasable couplers 114 from the implant 10. The actuator 116 may be slid to deflect the releasable couplers 114 from the implant 10 to release the releasable couplers 114 from the implant 10. The button of the actuator 116 may be pressed in a distal direction relative to the holder body 112 to slide the deflection surfaces 166 relative to the releasable couplers 114 to deflect the releasable couplers 114 from the implant 10 to release the releasable couplers 114 from the implant 10. The implant 10 may drop into the container that may include a fluid for moisturizing the implant 10 in embodiments.

The implant 10, released from the holder 110, may then be utilized for implantation. For example, a crimping procedure, utilizing the crimping device 84 shown in FIGS. 6 and 7 may be utilized. The implant 10 may be crimped to a delivery apparatus 44, and particularly to an implant retention area 54 of the delivery apparatus as shown in FIGS. 4 and 5. The delivery apparatus 44 and implant 10 may be positioned within the channel 90 of a crimping device 84 and may be crimped within the channel. The implant 10 may be delivered to an implantation site for implantation using the delivery apparatus 44. In other embodiments, other forms of device preparation and implantation may be utilized.

The holder, as disclosed herein, may be varied in embodiments. For example, the configuration of grip portions may be varied in embodiments, and may have varied shapes and other configurations than shown in FIGS. 8-12 for example. In embodiments, the configuration of the releasable couplers may be varied from the configuration shown in FIGS. 8-12. For example, various forms of latches, grippers, clamps, or other forms of couplers may be utilized in embodiments. The method of coupling to the implant may be varied in embodiments. The configuration of the actuator may be varied in embodiments. The actuator may cause the releasable couplers to release from the implant in a variety of manners. The actuator, for example, in embodiments, may be configured to be pulled, twisted, mechanically or electrically activated, or deformed (including snapping or breaking) to cause the releasable couplers to release from the implant. Various other configurations of the holder, and the holder body may be provided as desired.

Further, the method steps as disclosed herein may be varied as desired.

The holder, as disclosed herein, may beneficially improve the retention of the implant 10 and may improve the release of the implant 10 from the holder. For example, a user may relatively easily operate the actuator 116 to release the implant 10 from the holder. The holder may suspend the implant 10 in position for sterilization and transportation.

In embodiments, the holder may comprise a holder clip as disclosed herein, which may engage a portion of the implant 10 to hold the implant 10. The holder as disclosed herein may be handheld and portable, and configured to be transported to transport the implant 10 coupled thereto. The holder may be configured to be manipulated and controlled via handheld operation or via a device such as a clamp or another grasping device. The holder as disclosed herein may be utilized for transport or storage of the implant 10 as desired. Such transport or storage may occur prior to implantation of the implant 10 within the patient's body, or prior to a crimping or device preparation step that may occur prior to implantation.

The holder as disclosed herein may beneficially allow for a single step operation, in which the actuator may be operated in a single step. For example, as shown in FIGS. 15 and 16, a single step operation of the actuator may occur, in which the actuator is pressed in a direction to release the implant 10. Such a single step release may improve the ease in which the holder is utilized. Other forms of single step operation may include a single pull, twist, mechanical or electrical activation, or deformation, among other single step operations.

The holder may be positioned at an end of the implant 10 with the implant and holder having their longitudinal axes aligned, and the implant 10 extending longitudinally away from the holder. As such, the outer surface of the implant 10, and the "soft" components as disclosed herein may be exposed for sterilization, to improve the sterilization of such components. The holder may be positioned at an end of the implant 10 that is opposite the position of the skirt 20 as shown in FIG. 1 and in a direction towards which the leaflets 18*a-c* open in operation.

The implant 10 in embodiments, may comprise a medical implant such as an implantable prosthetic valve or another form of implant. The implantable prosthetic valve may comprise an implantable prosthetic heart valve in embodiments, such as a prosthetic aortic, pulmonary, mitral, or tricuspid valve. Various other forms of implantable prosthetic valves may be utilized, and various other forms of implants may be utilized in embodiments.

As discussed, various forms of implants may be utilized with the embodiments disclosed herein, including prosthetic heart valves, or other forms of implants, such as stents or filters, or diagnostic devices, among others. The implants may be expandable implants configured to move from a compressed or undeployed state to an expanded or deployed state. The implants may be compressible implants configured to be compressed inward to have a reduced outer profile and to move the implant to the compressed or undeployed state. A crimping device as disclosed herein may assist in moving the implant to the compressed or undeployed state.

The delivery apparatuses as disclosed herein may be utilized for aortic, mitral, tricuspid, and pulmonary replacement and repair as well. The delivery apparatuses may comprise delivery apparatuses for delivery of other forms of implants, such as stents or filters, or diagnostic devices, among others.

The delivery apparatuses and the systems disclosed herein may be used in transcatheter aortic valve implantation (TAVI) or replacement of other native heart valves (e.g., mitral, tricuspid, or pulmonary). The delivery apparatuses and the systems disclosed herein may be utilized for transarterial access, including transfemoral access, to a patient's heart. The delivery apparatuses and systems may be utilized in transcatheter percutaneous procedures, including transarterial procedures, which may be transfemoral or transjugular. Transapical procedures, among others, may also be utilized. Other procedures may be utilized as desired.

Features of embodiments may be modified, substituted, excluded, or combined across embodiments as desired.

In addition, the methods herein are not limited to the methods specifically described, and may include methods of utilizing the systems and apparatuses disclosed herein. The steps of the methods may be modified, excluded, or added to, with systems, apparatuses, and methods disclosed herein.

The features of the embodiments disclosed herein may be implemented independently of the crimping devices, or independent of other components disclosed herein. The various apparatuses of the system may be implemented independently.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of systems, apparatuses, and methods as disclosed herein, which is defined solely by the claims. Accordingly, the systems, apparatuses, and methods are not limited to that precisely as shown and described.

Certain embodiments of systems, apparatuses, and methods are described herein, including the best mode known to the inventors for carrying out the same. Of course, variations on these described embodiments will become apparent to those of ordinary skill in the art upon reading the foregoing description. The inventor expects skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described embodiments in all possible variations thereof is encompassed by the systems, apparatuses, and methods unless otherwise indicated herein or otherwise clearly contradicted by context.

Groupings of alternative embodiments, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses an approximation that may vary, yet is capable of performing the desired operation or process discussed herein.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A holder system for an implantable prosthetic valve, the holder system comprising:
   a holder body;
   one or more releasable couplers coupled to the holder body and configured to retain the implantable prosthetic valve to the holder body; and
   an actuator coupled to the holder body and configured to be operated to release the one or more releasable couplers from the implantable prosthetic valve, wherein the actuator is configured to slide within the holder body to release the one or more releasable couplers from the implantable prosthetic valve.

2. The holder system of claim 1, wherein the holder body includes one or more grip portions.

3. The holder system of claim 2, wherein the one or more grip portions comprise one or more arms.

4. The holder system of claim 2, wherein the one or more grip portions are configured to be gripped with a hand or gripped with a clamp.

5. The holder system of claim 2, wherein the one or more grip portions extend radially outward from a central portion of the holder body.

6. The holder system of claim 1, wherein the holder body includes a contact surface for contacting a portion of the implantable prosthetic valve.

7. The holder system of claim 6, wherein the contact surface is configured to contact an end of the implantable prosthetic valve.

8. The holder system of claim 1, wherein the holder body includes a recess for receiving a portion of the implantable prosthetic valve.

9. The holder system of claim 1, wherein the actuator is configured to be moved to release the one or more releasable couplers from the implantable prosthetic valve.

10. The holder system of claim 1, wherein the actuator is configured to slide to deflect the one or more releasable couplers from the implantable prosthetic valve to release the one or more releasable couplers from the implantable prosthetic valve.

11. The holder system of claim 1, wherein the holder body includes a central cavity for receiving the actuator.

12. The holder system of claim 11, wherein the actuator is configured to slide within the central cavity to release the one or more releasable couplers from the implantable prosthetic valve.

13. The holder system of claim 1, wherein the one or more releasable couplers comprise one or more hooks configured to engage a frame of the implantable prosthetic valve.

14. The holder system of claim 1, wherein the holder body includes a proximal portion and a distal portion for contacting the implantable prosthetic valve, and the one or more releasable couplers extend in a distal direction to engage the implantable prosthetic valve.

15. The holder system of claim 14, wherein the actuator includes a button and one or more deflection surfaces, and the button is configured to be pressed in a distal direction relative to the holder body to slide the one or more deflection surfaces relative to the one or more releasable couplers to deflect the one or more releasable couplers from the implantable prosthetic valve to release the one or more releasable couplers from the implantable prosthetic valve.

16. The holder system of claim 1, wherein the one or more releasable couplers include a plurality of releasable couplers spaced from each other.

17. The holder system of claim 1, further comprising a container configured to retain the holder body and the implantable prosthetic valve coupled to the one or more releasable couplers.

18. The holder system of claim 17, wherein the container includes a cavity and one or more interior surfaces defining the cavity, and the holder body is configured to couple to the container such that the holder body suspends the implantable prosthetic valve within the cavity.

19. The holder system of claim 18, wherein the container includes a gas permeable lid configured to cover the cavity.

* * * * *